US00PP36042P2

(12) United States Plant Patent
Kordes

(10) Patent No.: US PP36,042 P2
(45) Date of Patent: Jul. 30, 2024

(54) MINIATURE ROSE PLANT NAMED 'KORpot128'

(50) Latin Name: *Rosa hybrida*
Varietal Denomination: KORpot128

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/397,287

(22) Filed: Dec. 27, 2023

(51) Int. Cl.
*A01H 5/02* (2018.01)
*A01H 6/74* (2018.01)

(52) U.S. Cl.
USPC ..... Plt./121

(58) Field of Classification Search
USPC ..... Plt./101, 116, 121
See application file for complete search history.

(56) References Cited

U.S. PATENT DOCUMENTS

PP24,962 P2 10/2014 Kordes

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot128', is described. The new variety forms in abundance on a substantially continuous basis attractive, deep pink-colored blossoms. Double, cup-like rosette flowers are exhibited. The vegetation is vigorous, and the growth habit is compact. Attractive ornamental semi-glossy foliage is formed.

1 Drawing Sheet

Latin name of genus and species of plant claimed: *Rosa hybrida.*

Variety denomination: 'KORpot128'.

STATEMENT REGARDING PRIOR DISCLOSURES BY THE INVENTOR

The first offer for sale of the new variety was February 2023. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of miniature rose plant of the present invention was created by controlled breeding in 2019 in Offenseth-Sparrieshoop, Germany by artificial pollination wherein two parents were crossed which previously had been studied in the hope that they would contribute the desired characteristics. The female parent (i.e., the seed parent) of the new variety was an unnamed variety (not patented) which was the product of the cross between 'RUId244a' (not patented) and 'KORpot033' (U.S. Plant Pat. No. 24,962). The male parent (i.e., the pollen parent) of the new variety was an unnamed variety (not patented) which was the product of the cross between 'KORpot061' (not patented) and 'KORpot039' (not patented).

The parentage of the new variety can be summarized as follows:

('RUId244a' x 'KORpot033') x ('KORpot061' x 'KORpot039')

The seeds resulting from the above pollination were sown and small plants were obtained which were physically and biologically different from each other. Selective study resulted in the identification of a single plant of the new variety.

The new variety has been found to undergo asexual propagation at Klein Offenseth-Sparrieshoop, Germany by a number of routes such as vegetative cuttings. Asexual propagation techniques in Klein Offenseth-Sparrieshoop, Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of miniature rose plant of the present invention possesses the following combination of characteristics:

(a) forms attractive, deep pink-colored blossoms,
(b) exhibits a compact growth habit, and
(c) provides vigorous vegetation.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the unnamed seed parent variety (i.e., the product of ('RUId244a' x 'KORpot033')) taller growth habit and smaller flower size. Additionally, the new variety provides a smaller leaf size and larger flower size compared to the unnamed pollen parent variety (i.e., the product of ('KORpot061' x 'KORpot039')). Moreover, the new variety can be readily distinguished from non-parental related similar varieties. For example, the 'KORpot039' variety (not patented) displays a smaller flower size and more flowers per stem compared to the new variety.

The new variety has been named the 'KORpot128' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately twelve weeks of age and was grown indoors on its own roots in a 10.5 cm container in Odense, Denmark.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a one-year-old specimen of the new variety, observed during September, while growing in a one-gallon container on its own roots in a greenhouse in Cochranville, Pennsylvania.

Botanical classification: *Rosa hybrida* cultivar 'KORpot128'.

Commercial classification: Miniature Rose.

Plant:

*Habit*.—Compact.

*Height*.—Approximately 39.0 cm on average from the top of the soil plane in a 1-gallon container.

*Width*.—Approximately 34.0 cm on average.

Branches:

*Stem color*.—Commonly Green Group 143B.

*Length*.—Main stems: approximately 39.0 cm on average. — secondary stems: approximately 20.0 cm on average.

*Diameter*.—Main stems: approximately 7.0 mm on average. — secondary stems: approximately 3.0 mm on average.

*Texture*.—Glabrous.

*Thorns*.—Young thorns: amount is very few and small; length is approximately 2.0 mm on average; width is approximately 1.0 mm on average at point of attachment; and color is commonly Yellow-Green Group N144A. — old thorns: amount is moderate; length is approximately 5.0 mm on average; width is approximately 2.0 mm on average at point of attachment; and color is commonly Grey-Brown Group 199C.

Leaflets:

*Number*.—3, 5 and 7.

*Shape*.—Ovate; apex is acute; and base is rounded.

*Arrangement*.—Odd-pinnate.

*Margin*.—Serrate.

*Undulation*.—Moderate/medium.

*Glossiness of upper side*.—Semi-glossy.

*Texture*.—Upper surface: smooth. — under surface: smooth.

*Venation pattern*.—Reticulate.

*Size*.—Terminal leaflet: length is approximately 4.2 cm on average; width is approximately 2.0 cm on average. — lower leaflets: length is approximately 3.1 cm on average; width is approximately 1.7 cm on average. — 5-Leaflet leaf: length is approximately 9.0 cm on average; width is approximately 5.8 cm on average.

Foliage:

*Young foliage*.—Upper surface color: commonly Green Group 137C with indistinguishable venation. — under surface color: commonly a blend of Yellow-Green Group 148A and Greyed-Orange Group 176C with venation of Yellow-Green Group 146C.

*Old foliage*.—upper surface color: commonly Green Group 143C and Red-Purple Group 60A along margins with venation of Green Group 143A. — under surface color. commonly Green Group 138B and Red-Purple Group 60B around margins with indistinguishable venation.

*Petiole*.—Texture: upper surface is hispidulous; under surface is mostly smooth with sparse prickles. — length: approximately 1.7 cm on average. — width: approximately 1.0 mm on average. — upper surface color: commonly Green Group 138A. — under surface color: commonly Green Group 143A.

*Rachis*.—Length: approximately 1.5 cm on average. — width: approximately 1.0 mm on average. — upper surface color: commonly Green Group 137A. — under surface color: commonly Green Group 143A.

*Stipules*.—Length: approximately 8.0 mm on average. — width: approximately 2.0 mm on average. — margin: entire to erose. — upper surface color: commonly Green Group 141B. — lower surface color: commonly Green Group 143A.

Inflorescence:

*Number of flowers*.—About 12 to 15 blooms on average on a plant at once.

*Number of blossoms per stem or in a cluster*.—Typically 1 to 3 blooms per stem on average.

*Peduncle*.—Color: commonly Yellow-Green Group 144A. — diameter: approximately 2.0 mm on average. — length: approximately 2.8 cm on average. — surface texture: hispidulous. — strength: strong.

*Sepals*.—Number: 5. — upper surface color and texture: commonly Yellow-Green Group 144C toward center going to Green Group 138A out to the margins, covered in short pubescence. — under surface color and texture: commonly Green Group 143A, puberulent. — size: length is approximately 2.7 cm on average; width is approximately 6.0 mm on average. — margin: entire with occasional extensions on two or three sepals measuring approximately 4.0 mm in length and 1.0 mm in width on average; undulation is moderate/medium. — shape:

lanceolate. — apex: acute to aristate. — base: truncate or flat as it joins the receptacle.

*Buds*.—Shape: ovoid. — size: length is approximately 3.0 cm on average; width is approximately 1.2 cm on average. — color (when opening): commonly Red-Purple Group 60A.

*Flower*.—Form: double, cuplike rosette. — profile: cupped. — diameter: approximately 5.5 cm on average. — height: approximately 2.2 cm on average. — duration: on the plant approximately 20 days. — petal color when first and fully opened: upper surface is commonly Red-Purple Group 61B with a basal spot commonly of White Group 155A; under surface is commonly Red-Purple Group 60D with a basal spot commonly of White Group 155D. — petal color at end of bloom: upper surface is commonly Red-Purple Group 64B; under surface is commonly Red-Purple Group 64B. — petals reflex one by one: yes.

*Fragrance*.—Light sweet fragrance.

*Petal*.—Number: 17 on average. — drop: average for the type. — length: inner petals typically 2.5 cm; outer petals typically 3.1 cm. — width: inner petals typically 1.8 cm; outer petals typically 2.5 cm. — overall shape: broadly obovate. — margin: entire with medium undulation. — apex shape: rounded to cuspidate. — base shape: rounded to cuneate. — texture: upper surface is glabrous; under surface is glabrous.

*Petaloids*.—Number: 1 to 2. — length: approximately 1.2 cm on average. — width: approximately 5.0 mm on average. — color: upper and under surfaces are commonly Red-Purple Group 60C with a basal spot commonly of White Group 155A. — texture: smooth. — margin: variable, entire to erose. — shape: rounded and mostly curving inward. — apex: rounded. — base: cuneate.

*Stamen*.—Number: approximately 60. — anthers: number is approximately 60; color is commonly Yellow-Orange Group 20B; length is approximately 2.0 mm on average; and shape is oval. — filaments: length is approximately 4.0 mm on average and color is commonly Yellow Group 4D.

*Pistils*.—Arrangement: separate and free. — number: approximately 45. — style: length is approximately 5.0 mm and color is commonly White Group 155A at the base, transitioning to Red-Purple Group 70C at the apex. — stigma: diameter is less than 1.0 mm on average; shape is fan shaped; color is commonly White Group N155A.

*Receptacle*.—Diameter: approximately 6.0 mm on average. — shape: urn shaped. — color: commonly Yellow-Green Group 144A. — surface texture: smooth.

*Pollen*.—None observed.

*Hips/seed*.—None observed.

Development:

*Vegetation*.—Dark green, vigorous and strong.

*Blossoming*.—Abundant and continuous; blooms may continue year-round if grown inside a warm greenhouse.

*Resistance to diseases*.—Good resistance for powdery mildew (*Sphaerotheca pannosa*) under normal greenhouse growing conditions in Cochranville, Pennsylvania.

*Hardiness*.—Unknown.

The new 'KORpot128' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of miniature rose plant named 'KORpot128' characterized by the following combination of characteristics:

(a) forms attractive, deep pink-colored blossoms, (b) exhibits a compact growth habit, and (c) provides vigorous vegetation;

substantially as herein shown and described.

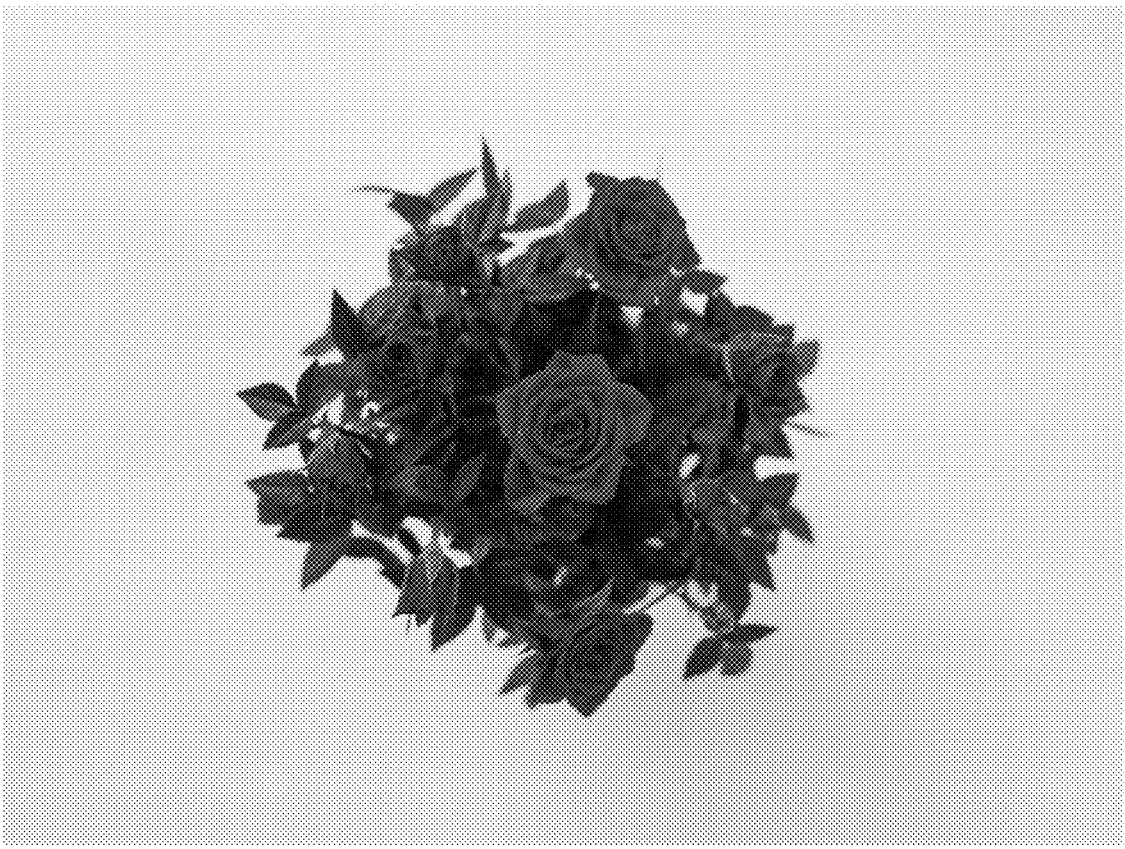

* * * * *